United States Patent [19]
Abbott et al.

[11] Patent Number: 6,007,823
[45] Date of Patent: Dec. 28, 1999

[54] SIMMONDSIN CONCENTRATE FROM JOJOBA

[75] Inventors: Thomas P. Abbott, Peoria, Ill.; Brian J. Plattner, Reynoldsburg, Ohio; Hal C. Purcell, Avila Beach, Calif.

[73] Assignee: The United States of America as represented by the Secretary of Agriculture, Washington, D.C.

[21] Appl. No.: 09/089,104

[22] Filed: Jun. 2, 1998

[51] Int. Cl.⁶ .................................................. A61K 35/78
[52] U.S. Cl. ...................... 424/195.1; 426/430; 426/478; 426/484
[58] Field of Search .................. 424/195.1; 426/430, 426/478, 484

[56] References Cited

U.S. PATENT DOCUMENTS

| | | | |
|---|---|---|---|
| 3,919,432 | 11/1975 | Elliger et al. | 426/319 |
| 4,148,928 | 4/1979 | Sodini et al. | 426/430 |
| 4,209,539 | 6/1980 | Banigan et al. | 426/319 |
| 5,672,371 | 9/1997 | D'Oosterlynck | 426/430 |

OTHER PUBLICATIONS

Abbot, T. P. et al., "Process for Making Animal Feed and Protein Isolates from Jojoba Meal", Jour. of Agric. & food Chem. 39(8):1488–1493, Mar. 1991.

Cotageorge, A. G, et al., "Detoxification of Jojoba Meal", Proceedings, 3rd International Conference on Jojoba, Sep. 13–16 1978, Univ. of California, Riverside, CA 92521.

Erhan, Selim et al., "Simmondsin Concentrate from Defatted Jojoba Meal", Industrial Crops and Products 6:147–154, May 1997.

Hassaneen, Nagwa Zaki Sadek, "Extraction of Oilssed Model Systems with Alcohols", Dissertation Grad. College of Texas A&M Univ., Aug. 1985.

Lanzani, A., "A Wet Process Technology Applied to Jojoba Seed to Obtain Oil and Detoxified Protein Meal", JAOCS 60 (10): 722–774, Oct. 1991.

Medina, L. et al., "detoxified and Debittered Jojoba Meal: Biological Evaluation and Physical–Chemical Characterization", Cereal Chemistry 67 (5) :476–479, Sep. 1990.

Abbott, T. P. et al., "Processing Jojoba Meal as Animal Feed", Jour. of Diary Sci. 72 (Suppl 1) ;563–564, Aug. 1989.

Manos, C. G., "Developments on Use of Jojoba Meal as Animal Feed", JAOCS 65 (1) :36, Jan. 1988.

Van Boven, M. et al., "Isolation, Purification and Stereochemistry of Simmondsin", Jour. of Agric & Foood Chem. 41 (10) : 1605–1607, Oct. 1993.

Van Boven, M. et al. "Isolation and Structure Elucidation of the Major Simmondsin Analogues in Jojoba Meal by Two–Dmensional NMR Spectroscopy", Jour. of Agric. & Food Chem. 42 (12): 2684–2687, Dec. 1994.

Van Boven, M. et al., "New Simmondsin 2'–Ferulate from Jojoba Meal", Jour. of Agric. & Food Chem. 43 (10) : 1193–1197, May 1995.

Van Boven, M. et al., "Determination of Simmondsins and Simmondsin Ferulates in Jojoba Meal and Feed by High–Performance Liquid Chromotography", Jour. of agric. & Food Chem. 44 (8) : 2239–2243, Aug. 1996.

Verbiscar, A. et al., "Detoxification of Jojoba Meal", Jour. of Agric. & food Chem. 28 (3): 571–578, 1980.

Hassanen, Nagwa Zaki Sadek, "Extraction of Oilsee Model Systems with Alcohols", Dissertation submitted to Grad. College of Texas A&M Univ., Aug. 1985.

Erhan, Selim, et al., "Simmondsin concentrate from defatted jojoba meal", Industrial Crops and Products, 1997, 6, pp. 147–154.

Cotageorge, A.G., et al., Detoxification of Jojoba Seed Meal, Proceedings, 3rd International Conference on Jojoba, Sep. 13–16, 1978, Univ. Of California, Riverside, CA 92521.

Verbiscar. Anthony, et al., "Detoxification of Jojoba Meal", J. Agric. Food Chem. 1980, 28, pp. 571–578.

Primary Examiner—Jean C. Witz
Assistant Examiner—Angela N. Trafton
Attorney, Agent, or Firm—M. Howard Silverstein; Randall E. Deck; John D. Fado

[57] ABSTRACT

A process for the isolation of simmondsins from jojoba meal is disclosed. Simmondsins are first extracted from defatted jojoba meal with water. After separation from the meal, this water extract is subsequently dried, leaving the simmondsins in the resulting solid. The simmondsins may then be preferentially extracted from the dried water extract by contact with a first ethanolic solvent, forming a first solvent fraction containing simmondsins therein. The first solvent fraction, which is a substantially protein-free concentrate of simmondsins, may be separated from the solid phase, and the ethanolic solvent may then be readily removed, for example, by drying. Residual simmondsins remaining in the meal following extraction with the first ethanolic solvent may also be recovered by a second extraction with ethanolic solvent. Optionally, simmondsin and its analogs, simmondsin ferulate, demethylsimmondsin, and didemethyl simmondsin, may be separated in substantially pure form from the extracts by reverse-phase HPLC.

14 Claims, 5 Drawing Sheets

SIMMONDSIN CONCENTRATE FROM JOJOBA

BACKGROUND OF THE INVENTION

1. Field of the Invention

The invention relates to a novel process for extracting and separating simmondsins from jojoba meal.

2. Description of the Prior art

Jojoba, Simmondsia chinensis (Link) Schneider, is native to the desert Southwestern United States and Mexico. It is currently being grown on 8,000 to 12,000 acres in the U.S. and elsewhere worldwide. Jojoba has a unique wax ester oil which is 50 to 60% of its seed weight. This oil is currently used in cosmetics and lubricants. The remainder of the seed is not used as much as the oil, even though it contains about 25% crude protein after the oil is removed. The defatted meal contains sugars and 11–15% of a unique group of natural products, all structurally related to simmondsin. Cokeleare et al. (1995, Ind. Crops Prod., 4:91–96) have shown that simmondsin is an effective hunger satiation agent and reduces food intake in mice, rats and chickens. Jojoba meal has been used for its simmondsin content to regulate food intake of animals, but the meal also contains other antinutritional factors such as trypsin inhibitor, polyphenols, bitter taste, nonnutritive protein and indigestible jojoba oil.

The isolation of simmondsin was first described by Elliger et al. (1973, J. Chem. Soc., Perkin Trans., 1:2209–2212) who extracted it with ethyl acetate from the ground seed whose oil had been removed with hexane. Many other solvent combinations have since been tested for removal of simmondsin and its analogues from the defatted (oil-free) ground seed meal, with the goal of complete extraction of all simmondsin analogues. Cotageorge et al. (1978, Detoxification of jojoba meal. In: Yermanos (Ed.), Proceedings of the Third International Conference on Jojoba, Riverside, Calif. University of California. pp. 171–184) used water, 90% ethanol and methanol. Water was found to extract all of the simmondsins but repeated extractions with methanol or 90% ethanol were insufficient to remove all of the simmondsins from the defatted jojoba meal. More recently, Erhan et al. (1997, Ind. Crops Prod., 6:147–154) disclosed a process for the water extraction of jojoba meal which produced a concentrate containing 42% simmondsin and related substances. Medina et al. (1988, Elimination of toxic compounds, nutritional evaluation and partial characterization of protein from jojoba meal. In: Baldwin (Ed.), Production, Processing and Utilization of Jojoba, Am. Oil Chem. Soc., Champaign, Ill., pp. 423–429) used isopropanol-water in various ratios to extract simmondsins and tannins from defatted meal. A ratio of 7:3 (isopropanol:water) was found to be optimal for total extraction of simmondsins and partial removal of tannins. Abbott et al. (1988, Monitoring jojoba toxins by Fourier transform infrared spectroscopy and HPLC, In: Baldwin (Ed.), Production, Processing and Utilization of Jojoba, Am. Oil Chem. Soc., Champaign, Ill., pp. 440–450) reported that a ratio of 9:1 acetonitrile:water extracted the simmondsins completely from defatted meal, and the same solvent could be used to separate the four simmondsin compounds—simmondsin (S), simmondsin ferulate (SF), demethylsimmondsin (DMS) and didemethyl simmondsin (DDMS) individually on an analytical chromatographic column. Verbiscar et al. (1980, J. Agric. Food Chem., 28:571–578) tested acetone, isopropanol, methanol, dichloromethane:methanol in the ratio of 85:15 and water to extract simmondsin or simmondsin ferulate from defatted meal and found that only water and methanol extracted simmondsin and simmondsin ferulate nearly completely. Acetone extraction, followed by preparative silica gel column separation with chloroform, acetone, and chloroform/methanol have been proposed for solvent-based preparation of simmondsin (Van Boven et al., 1993, J. Agric. Food Chem., 41:1605–1607). A similar procedure was used to prepare mg quantities of demethylsimmondsin and didemethyl simmondsin (Van Boven et al., 1996, Isolation by preparative HPLC of simmondsin analogues from jojoba meal, In: Princen and Rossi (Ed.), Proceedings of the IX International Conference on Jojoba and Its Uses, Sep. 26–30, 1994, Catamarca, Argentina. Am. Oil Chem. Soc., Champaign, Ill., pp. 135–136). For quantitative extraction of simmondsin and simmondsin ferulate from jojoba meal and feed samples, methanol or 80/20 acetonitrile/water was found to work best and 1-propanol or other mixtures of acetonitrile and water did not work as well in a column extraction or extraction tube method (Van Boven et al., 1996, J. Agric. Food Chem., 44:2239–2243). Membrane separation processes for isolating both the protein and the low molecular weight components have been reported (Abbott et al., 1991, J. Agric. Food Chem. 39:1488–1493. Abbott, et al., 1996, Processing jojoba meal for value-added products using membrane separations, In: Princen and Rossi (Ed.), Proceedings of the IX International Conference on Jojoba and Its Uses, Sep. 26–30, 1994, Catamarca, Argentina, Am. Oil Chem. Soc., Champaign, Ill., pp. 126–130; Nabetani et al., 1995, Ind. Eng. Chem., 34:1779–1788). Sequential extraction of jojoba meal with isopropanol removed primarily oil in the first sequence and reduced simmondsin and analogues concentration in the meal in a second sequential extraction but ethanol was not suitable for sequential extractions (Hassanen, 1985 Extraction of oilseed model systems with alcohols, PhD Thesis, Texas A&M University, College Station, Tex.).

SUMMARY OF THE INVENTION

We have now discovered a novel process for the selective extraction of simmondsins from jojoba meal at high yields. Simmondsins are first extracted from defatted jojoba meal with water. After separation from the meal, this water extract is subsequently dried, leaving the simmondsins in the resulting solid. The simmondsins may then be preferentially extracted from the dried water extract by contact with a first ethanolic solvent, forming a first solvent fraction containing simmondsins therein. The first solvent fraction, which is a substantially protein-free concentrate of simmondsins, may be separated from the solid phase, and ethanolic solvent may then be readily removed, for example, by drying. Residual simmondsins remaining in the meal following extraction with the first ethanolic solvent may also be recovered by a second extraction with ethanolic solvent. Optionally, simmondsin and its analogs, simmondsin ferulate, demethylsimmondsin, and didemethyl simmondsin, may be separated in substantially pure form from the extracts by reverse-phase HPLC.

In accordance with this discovery, it is an object of this invention to provide an improved method for isolating simmondsins from jojoba meal.

It is another object of the invention to provide a method for extracting simmondsins from jojoba meal in a highly concentrated composition and at high yields.

Yet another object of the invention is to provide a method for the isolation and purification of high yields of each of simmondsin, simmondsin ferulate, demethylsimmondsin, and didemethyl simmondsin, from jojoba meal.

Still another object of the invention is to provide a method for the isolation of simmondsins which minimizes the use of toxic solvents.

Other objects and advantages of this invention will become readily apparent from the ensuing description.

DETAILED DESCRIPTION

Figure 1:
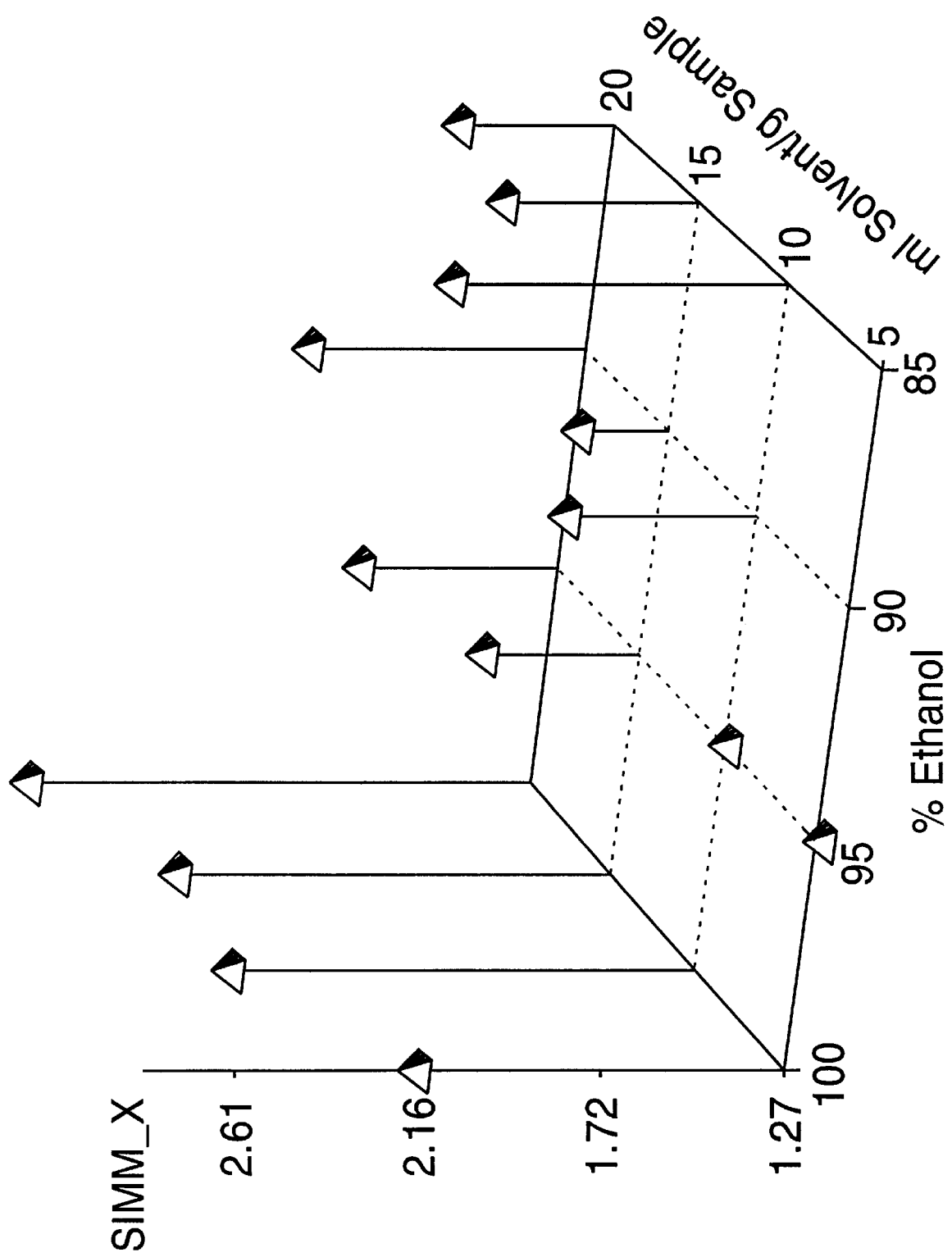
FIG. 1 shows the enrichment of simmondsin (SIMM_X, the product of the amount and purity of simmondsin extracted relative to the starting material) in ethanol/water extracts at various ratios of solvent volume to sample weight of simmondsin concentrate.

The preferred starting material for use in the invention is the dried water extract of defatted meal of jojoba, Simmondsia chinensis (Link) Schneider. However, it is envisioned that extracts of other tissues of the plant would also be expected to contain simmondsins subject to enrichment and purification by the same invention process. The process for the water extraction of simmondsins from defatted meal is described in detail by Erhan et al. (1997, Industrial Crops and Products, 6:147–154), the contents of which are incorporated by reference herein.

In review, jojoba meal is initially defatted, that is waxes and oils are separated from the meal, using conventional techniques such as pressing and/or solvent extraction. A combination of screw pressing of the ground meal followed by hexane extraction is generally preferred. The defatted ground meal is then contacted or washed one or more times with water, preferably with agitation, for a sufficient time to extract the simmondsins from the meal. The solids and water extract containing simmondsins are then separated. Without being limited thereto, suitable separation techniques include settling, filtration, and combinations thereof. The solid meal having simmondsins removed therefrom may be discarded or retained for use as a fuel or cattle feed (Vontungelin et al., 1997, J. Anim. Sci. Suppl. 1, 75:26). The aqueous supernatant or water extract is retained and treated to remove the water therefrom. Suitable techniques for water removal include but are not limited to heat and/or vacuum evaporation, spray drying, or reverse osmosis concentration, with the combination of reverse osmosis concentration followed by spray drying being preferred. The resultant solid which contains concentrated simmondsins is referred to as the dried water extract.

Although water extraction solvates and concentrates the simmondsins, water is not selective for these compounds but also extracts a variety of undesirable soluble proteins, sugars, plant hormones, and polysaccharides from the jojoba meal. Thus, the dried water extract may still contain only approximately 40% simmondsins by weight, in combination with these other jojoba components. We have discovered that the simmondsins may be selectively extracted from the dried water extract, and in high yield, by extraction with ethanolic solvents.

In accordance with this invention, the dried water extract is contacted with the ethanolic solvent at a concentration and volume, and under conditions effective for the selective extraction of the simmondsins, with no or substantially no solvation of the proteins in the meal.

The ethanol concentration (weight %) of the solvent, which may also be expressed as the ethanol:water ratio, is critical for the selective or preferential extraction of the simmondsins over jojoba proteins and sugars. To effect selective extraction of simmondsins, the ethanol concentration should be greater than or equal to about 80% (80:20 ethanol:water). In the preferred embodiment, the ethanol concentration should be greater than or equal to 95%, with about 100% or absolute ethanol being particularly preferred. Extracts obtained using absolute ethanol contain no detectable proteins. In contrast, concentrations less than 80% exhibit decreased selectivity for simmondsins and solubilize significant amounts of proteins and sugars. Furthermore, the relative selectivity of the solvent toward one or more of the specific simmondsins (simmondsin, simmondsin ferulate, demethylsimmondsin, or didemethyl simmondsin) may be manipulated by variation of the ethanol concentration of the solvent between about 80-100%. For instance, use of absolute ethanol provides the greatest selective extraction of simmondsin and simmondsin ferulate and is therefore preferred. In fact, the selective extraction of simmondsin with absolute ethanol is far superior than that achieved using solvents containing 95% or less ethanol. In contrast, use of 95% ethanol provides the greatest selective extraction of demethylsimmondsin, while 80% ethanol provides the greatest selective extraction of the non-bioactive analog, didemethyl simmondsin.

Extraction of the simmondsins may vary not only with the ethanol concentration of the solvent, but also with its volume. As described in greater detail in Example 1, the greatest selective extraction of simmondsin is achieved using absolute ethanol at a ratio of solvent:dried water extract of about 20:1 (ml solvent:g solute), while the greatest selective extraction of simmondsin ferulate with this same solvent is at a ratio of about 5:1 or less. The precise volume of solvent used may be readily selected by the skilled practitioner and will vary with the ethanol concentration and the particular simmondsin(s) desired for extraction (i.e. simmondsin or its analogs). However, in accordance with the preferred embodiment, the ratio of solvent:dried water extract is between about 1:1 to 20:1, particularly about 5:1 to 20:1, and is most preferably about 20:1. The skilled practitioner will also recognize that the use of higher solvent volumes may be impractical.

The dried water extract is typically contacted with the ethanolic solvent using conventional techniques, for example, by stirring, or diffusion through a filtration barrier such as cloth or filter thimbles. The length of time for this contact will vary with the concentration and amount of the solvent, the sample size, and the particular technique of contacting used. Generally, this time may be as little as about 15 minutes or up to a sufficient period of time for equilibration, usually one to four hours. The extraction solvent should be sealed from ambient air, particularly when using absolute ethanol, to prevent water absorption by the ethanol and a consequential change in the solvent's selectivity for simmondsins over proteins and sugars. Temperature of extraction is typically ambient but higher and lower temperatures appear to have little or no effect on selectivity of salvation or amount dissolved. Following extraction, the solvent fraction containing the extracted simmondsins is separated from the insoluble solids, for example, by centrifugation, decantation, or filtration. This solvent fraction is retained, and solvent may be removed therefrom using a variety of techniques, including but not limited to spray drying, distillation, vacuum oven drying, rotating solvent evaporation, or a combination thereof. Ethanolic solvents recovered from the drying process may be recycled to the extractors. It is understood that the process is not limited to the extraction of the dried water extract with a single volume of solvent, but that the dried water extract may be extracted sequentially with two or more volumes of fresh ethanolic solvent and the extracts combined.

The solid or simmondsin concentrate remaining after removal of solvent from the solvent fraction is a composition of highly concentrated simmondsins free or substantially free of jojoba proteins. Using absolute ethanol as solvent, we have produced a simmondsin concentrate consisting of up to about 80% simmondsins with no detectable proteins. The simmondsin concentrate may be retained for use as a hunger satiation agent for reducing food intake in animals. Alternatively, simmondsin and its analogs in the concentrate may be further isolated and purified by high-pressure liquid chromatography (HPLC) as described hereinbelow.

The insoluble residue remaining after separation of the ethanolic solvent fraction may be further extracted with one or more additional ethanolic solvents for the removal of residual simmondsins in the same manner as above. However, in the preferred embodiment, extraction is conducted using a second solvent which is between about 70–95% ethanol, preferably about 80% ethanol. Extraction with 80% ethanol is effective for the nearly complete salvation of the remaining simmondsins with the concurrent solvation of only small amounts of protein. The solvent fraction containing simmondsins from this second extraction may also be recovered and solvent removed in the same manner as the first ethanolic extraction. Using a second solvent extraction with 80% ethanol in this manner, following a first extraction with absolute ethanol, we have obtained a second simmondsin concentrate containing up to about 41% simmondsins and only about 1–2% protein. Like the simmondsin concentrate from the first ethanolic extraction, the second simmondsin concentrate may be retained for use or subjected to further purification.

For further purification, the simmondsin concentrates may be separated by high-pressure liquid chromatography. The concentrates are dissolved in an approximately equal amount of water and injected onto a reversed phase, preparative scale HPLC column. Eluting solvent is programmed from 100% water to 100% ethanol and fractions collected. A sequence of 100% water, followed by 50% ethanol/50% water mixture, followed by 100% ethanol, is preferred. Compositions of the various fractions may be analyzed by analytical HPLC. Separation of the first simmondsin concentrate obtained using extraction with absolute ethanol, produced fractions containing greater than 90% pure simmondsin, simmondsin ferulate and demethylsimmondsin with didemethylsimmondsin. These fractions may be dried for use as described above.

The following examples are intended to further illustrate the invention and are not intended to limit the scope of the subject matter which is defined by the claims.

EXAMPLE 1

Materials and Methods

The dried water extract from defatted jojoba meal (DWE) was prepared as described by Erhan et al. (1997). All other reagents were ACS or HPLC grade.

Selective Solvation of Simmondsins

DWE, 1 gram, was stirred 30 min with 20 ml of either acetone, acetonitrile, chloroform, methanol, water, ethanol, isopropanol, 95/5 isopropanol/water or 5/95 methanol/chloroform. Supernatant was filtered, dried, weighed, and analyzed for simmondsin and analogues. After ethanol and isopropanol were found to selectively extract simmondsins, the temperature (16, 26, 36° C.), solvent volume to sample weight ratio, and amount of water in combination with ethanol or isopropanol were tested to determine the effect on enrichment of individual components and the amount of simmondsins dissolved compared to the same components in the DWE. Both the amount of simmondsins extracted and their enrichment in the extract are important in choosing a selective solvent. Therefore, selectivity was calculated as enrichment times concentration for each component, simmondsin, simmondsin ferulate, demethylsimmondsin and didemethyl simmondsin as well as the total for all four components and plotted against solvent composition and solvent to solute ratio. For simmondsin, selectivity or SIMM_X=[(concentration of simmondsin in extract)/(concentration of simmondsin in DWE)][weight of simmondsin in extract/weight of simmondsin in DWE].

A solvent that extracts all of the simmondsin from a sample and nothing else from a sample (DWE) with a composition of 15.3% simmondsin would have a selectivity of (100%/15.3%)(0.153/0.153)=6.54, meaning that all of the simmondsin is solubilized and its purity was increased by 6.54 times in the extract compared to the DWE. A solvent that extracts half of the simmondsin from the same sample and the extract is composed of 50% simmondsin and 50% other components would have a selectivity of (50%/15.3%)(7.65/15.3)=1.63. A solvent that dissolves the entire sample would have a selectivity of 1.0. Values less than one would indicate less of that component in solution but enrichment in the extracted residue. Similar calculations were made for all components to optimize extraction. Multiple ethanol extractions at the 10:1 volume:sample weight ratio were also tested at room temperature. Elution from a column of DWE with ethanol and soxhlet extraction with ethanol were also tested.

Analytical Tests

For simmondsin and analogues analysis, samples containing 15 mg of simmondsin and analogues (~15 mg of HPLC separated fractions or 40 mg of DWE) were mixed with deionized, organics-free water (25 ml) containing 2.00 ml/L benzyl alcohol in a Teflon-lined capped vial. The sample solutions were filtered through a 0.45 µm micro porous filter and 1 ml placed in autoinjection vials. A 3 µL sample was automatically injected onto a 4.6 mm×10 cm Hypersil ODS (C-18) 3U reversed phase column (ALTECH Associates, Inc.). Solvent was programmed from 0 to 100% methanol in an aqueous mix over 20 minutes at a flow rate of 0.75 mL/min, then held at 100% methanol for 5 min. The HPLC system (Thermo Separation Products) consisted of a Model AS3000 autoinjector, P2000 pump, column, and a UV2000 detector set at 220 nm and a 10 mm pathlength flow cell. Analysis time per sample, including re-equilibration, was typically 40 min. Elution time of simmondsin was 8.0 min, demethylsimmondsin 6.2 and 7.2 min (positional isomers), didemethyl simmondsin 2.9 min and simmondsin ferulate 12.8 and 13.2 min (cis, trans isomers). Peak areas were compared to a calibration curve made from authentic samples ratioed to the internal standard of benzyl alcohol (elution time 11.2 min), and concentrations in the original sample were calculated.

Preparative HPLC Separations

A C18, 55–105 µm PrepPak Cartridge was used in a Prep 500 Compression Module (Waters). The column was pre-conditioned by washing with 80/20 ethanol/water for 60 min at 50 ml/min. A blank run with no injection was made and then sample (10 g) in 50 ml water (filtered through a 0.5 µm filter) was injected onto the column. Solvent was programmed at 50 ml/min starting with 100% water from 0–50 min, then 50/50 water/ethanol from 50 to 60 min, and then 100% ethanol from 60 to 75 min. Fractions were collected at approximately 3 min intervals (150 ml) but similar fractions, based on HPLC analysis, were combined.

Results and Discussion

Selective Solvation

Table 1 shows the amount and composition of extracts of DWE in various solvents and mixtures of solvents. Many of the solvents previously tested for extraction of simmondsins from jojoba meal were tested on the water extract, but most failed to extract significant amounts of the simmondsins. Extraction of the water extract was significantly different from extraction of the meal. Acetone, acetonitrile and chloroform extracted it or less of the weight of the water extract in contrast to the prior art teaching that acetone is the solvent of choice for extraction of simmondsin from the meal. Methanol and water dissolved the extract nearly completely without selectivity. Methanol/chloroform 5/95 dissolved 8.6% of the water extract without differentiating of simmondsins and sugars or protein.

Ethanol, isopropanol and 95/5 isopropanol/water enriched simmondsin content and at the same time extracted a substantial portion of the total simmondsins present. Table 2 shows the weight of extract and extract composition for isopropanol/water combinations. Simmondsin concentration is highest in the 90/10 isopropanol/water extract at a solvent/solute ratio of 10 to 1. However, only 50 of the simmondsin in the DWE is extracted. Using the method described in the experimental section, a selectivity value was calculated (Table 3). The values for combinations of isopropanol and water in Table 3 indicate only a marginal advantage for 90/10 isopropanol/water when viewed with these values.

Figure 2:
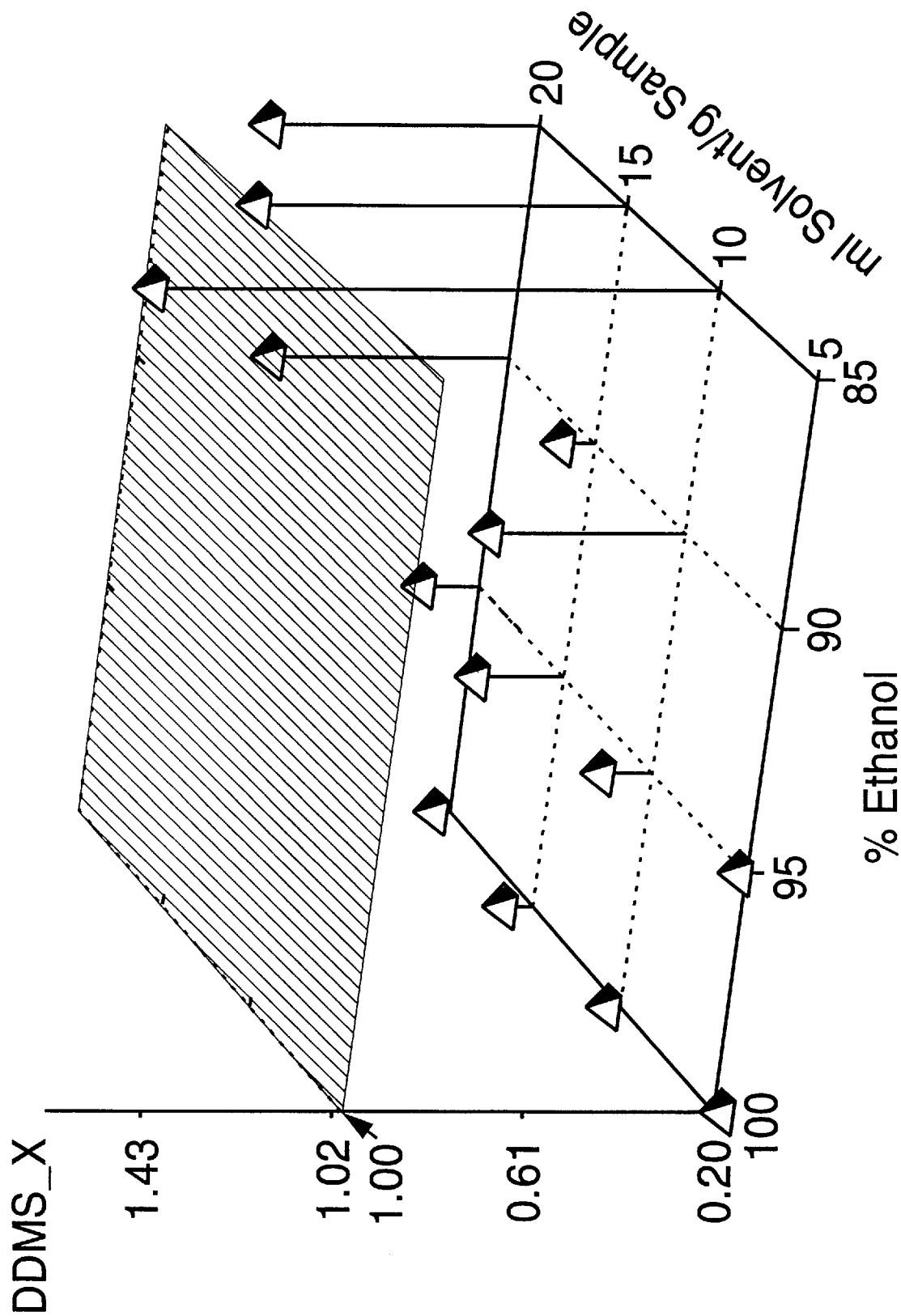
FIG. 2 shows the enrichment of simmondsin ferulate (SF_X) in ethanol/water extracts at various ratios of solvent volume to sample weight of simmondsin concentrate.
Figure 3:
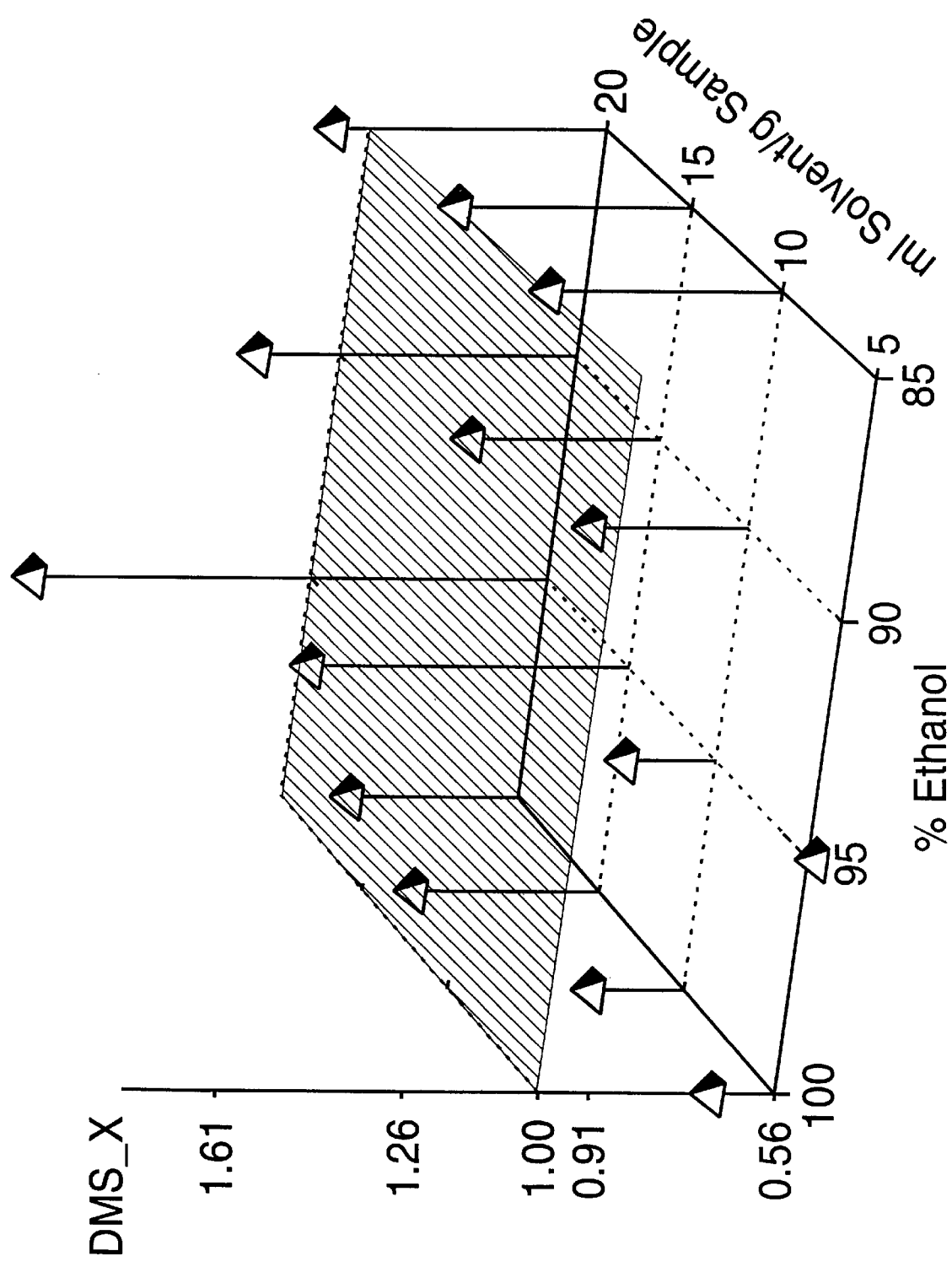
FIG. 3 shows the enrichment of demethylsimmondsin (DMS_X) in ethanol/water extracts at various ratios of solvent volume to sample weight of simmondsin concentrate.
Figure 4:
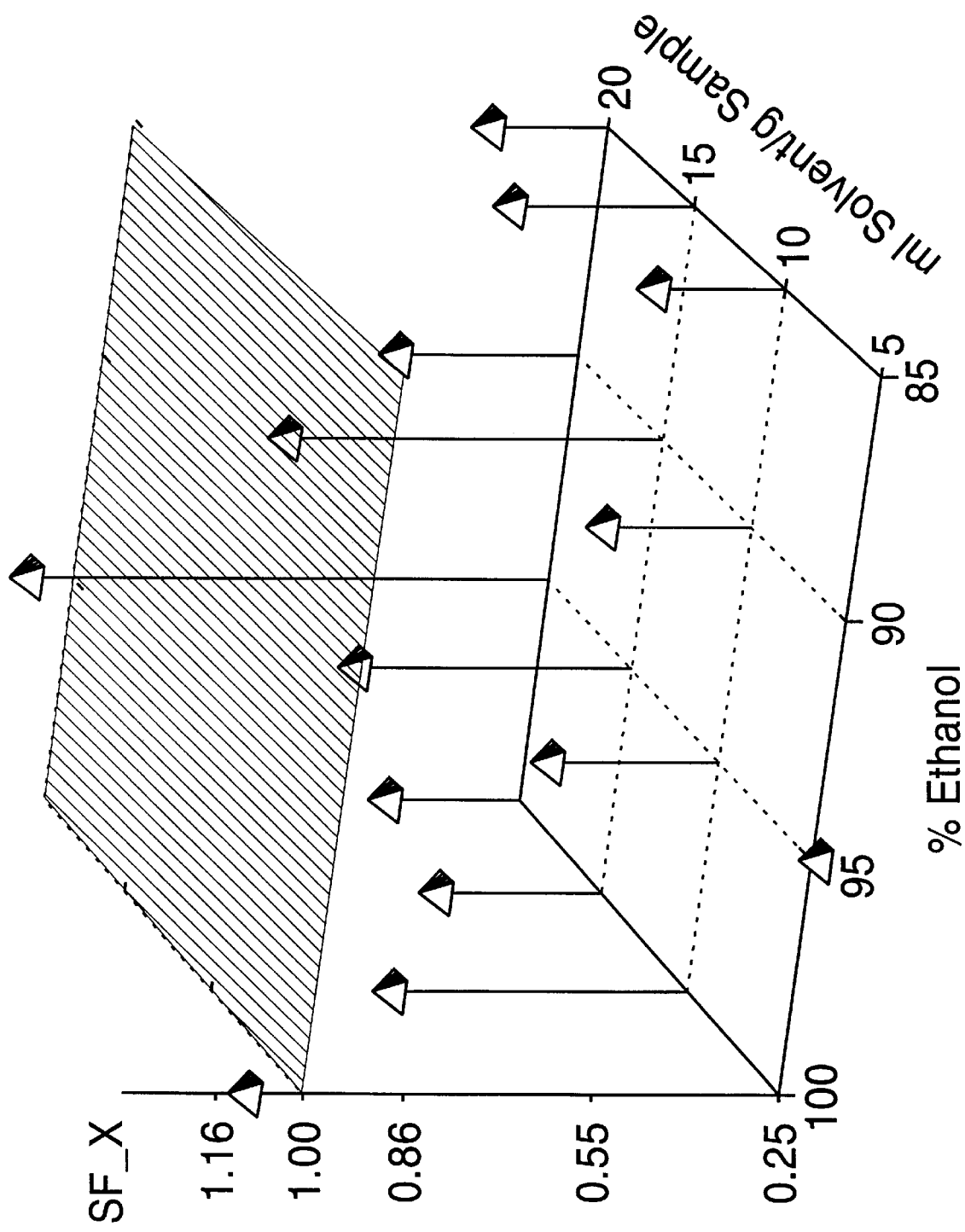
FIG. 4 shows the enrichment of didemethyl simmondsin (DDMS_X) in ethanol/water extracts at various ratios of solvent volume to sample weight of simmondsin concentrate.
Figure 5:
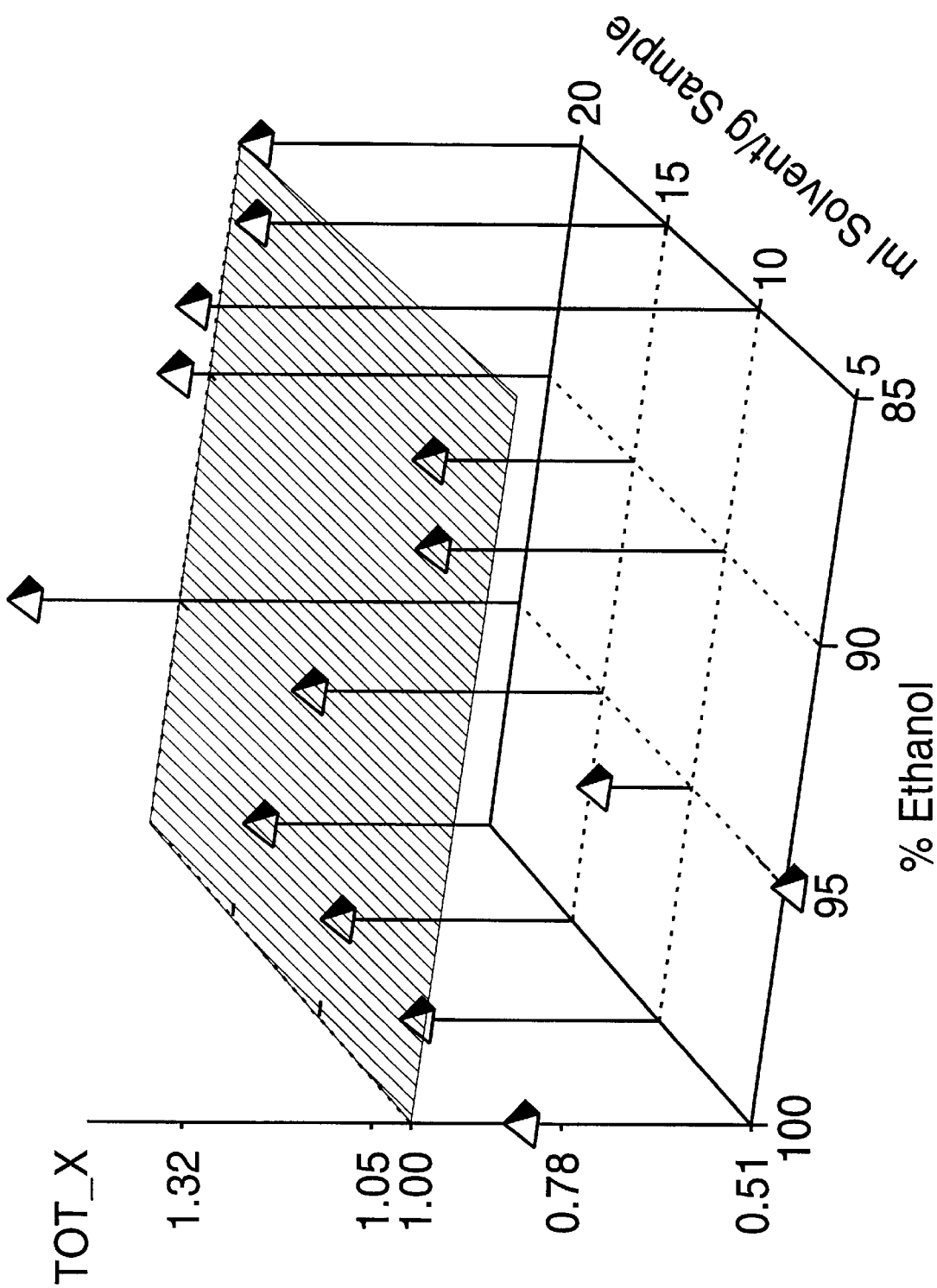
FIG. 5 shows the enrichment of total simmondsins (TOTL_X) in ethanol/water extracts at various ratios of solvent volume to sample weight of simmondsin concentrate.

Many ethanol-water combinations had much higher selectivity values, even though total simmondsins in 90/10 isopropanol/water reached 63% and in absolute ethanol total simmondsins never exceeded 72%. FIGS. 1–5 show the effect of water content and solvent to solids ratio on the weight and purity of each of the simmondsin analogues extracted by ethanol/water combinations. That is, the vertical axis is a measure of both purity of individual component and the amount of the available component that is extracted into the solvent. FIG. 1 shows that 100% ethanol, at a solvent volume to solute weight ratio of 20:1 gives the greatest enrichment of simmondsin, with a SIMM_X value of 2.61. For simmondsin ferulate (SF) smaller volume to sample weight ratios and absolute ethanol as solvent appears to be the best choice (FIG. 4); smaller solvent to solute ratios and increased water content are selective for didemethyl simmondsin (DDMS), giving a DDMS_X value of 1.43 for 85/15 ethanol/water at a 10:1 solvent:solute ratio (FIG. 2). Extraction of demethylsimmondsin (DMS) is optimal at 20:1 solvent to solute (95/5 ethanol/water) (FIG. 3) although 5:1 ethanol:solute is also selective for simmondsin ferulate. Higher water contents than 20% concomitant with higher solvent volumes led to complete sample solubilization, although a 10:1 solvent:solute ratio with 80/20 ethanol/water did not completely dissolve the sample.

Extracting DWE (2.0 g) sequentially with ethanol (20 ml), but removing only 15 ml and replacing it with fresh ethanol gave 69%, 70%, 65% and 64% simmondsins in four sequential extracts. Extract weight decreased in each extraction from 20 to 14 to 8.2 to 5.6% of the starting sample weight. Thus the first two extractions removed 34% of the sample weight and maintained a high concentration of desired components. However, the residue retained 17.2% simmondsins, principally didemethyl simmondsin even after 4 extractions with ethanol. This agrees with the data in FIG. 4 which shows that the solubility of didemethyl simmondsin in absolute ethanol is very limited. If, at some later time, didemethyl simmondsin is shown not to be efficacious for a desired product, countercurrent or sequential extraction with ethanol may prove to be a preferred method of recovery. Elution of a mixture of DWE (5 g) with ethanol in a column showed that after about 35 ml had eluted, 29% of the starting material had been eluted with the same composition as the ethanol extract in Table 1. Fractions collected after the first 35 ml contained less simmondsin, simmondsin ferulate and demethylsimmondsin and increasing amounts of didemethyl simmondsin. Further enrichment of samples with the composition of the ethanol extract Table 1 was not possible by further extraction of the dried material with ethanol or isopropanol. However, when a solution of the room temperature ethanol extract was evaporated on a rotating solvent evaporator to a concentration of 12% solids and stored overnight at 4° C., a precipitate formed. Separating the supernatant and the precipitate and analyzing the two showed that the supernatant contained nearly 100% simmondsins (lower didemethyl simmondsin) and the precipitates had increased amounts of didemethyl simmondsin and lower total simmondsins. This raises the possibility of crystallization of didemethyl simmondsin and polar impurities as an enrichment step.

Temperature dependence of extraction of DWE with ethanol/water combinations is shown in Table 4. Solubility of concentrate in both absolute ethanol and 85/15 ethanol/ water show significant dependence on temperature. However, when DWE (1 g) was extracted with ethanol (10 ml) at 68° C. and the supernatant cooled to −7° C. for 2 days, the supernatant contained 84% simmondsins and 25% of the weight of DWE. Sohxlet extraction with absolute ethanol followed by the azeotropic 95/5 ethanol/water extracted 38% of the sample weight, but left 23.9% simmondsins in the extracted residue. Experiments with 95/5 ethanol/water in the Sohxlet extraction gave 77% simmondsins in the extract, but extracted only 19% of the DWE by weight. None of the procedures utilizing temperature dependence of solubility were markedly better than room temperature procedures.

Extraction of DWE with ethanol (20:1 solvent volume:sample weight), followed by extraction with 80/20 ethanol/water (10:1) would enrich simmondsins in the first fraction, remove most of the remaining simmondsins in the second extract and leave a sugar residue with a low level of simmondsins. This solvent extraction sequence gave the results shown in Table 5 for 516 g of DWE extracted 24 hr with each solvent. The results were as predicted by the analytical separations, except that a slightly higher amount of solids was extracted in ethanol. The ethanol extract is suitable as a starting material for chromatographic separation and the 80/20 extract could be further refined or recycled into the DWE after water is removed. An analysis of the total and non-protein nitrogen in all three fractions showed that the ethanol extract has no protein, the 80/20 ethanol/water extract has 1.2% protein and the residue has 35.4% protein.

Preparative HPLC

Separation of the ethanol extract of simmondsin concentrate gave the fractions in Table 6. Of the 10 g starting material, 9.05 g were recovered. The starting material contained about 4% water and there were some losses on injection and in drying and transfer. Fraction 1 would be recombined with the sugars residue, fraction 4 was saved as an acceptable grade of pure simmondsin and fraction 7 was saved as an acceptable grade of pure simmondsin ferulate. This represents 77% of the recovered solids. Fractions 2 and 3 would be used to prepare demethylsimmondsin and didemethyl simmondsin and fractions 6 and 8 would be recycled into the DWE for a repeat extraction. Fraction 5 may be discarded, depending on a more thorough analysis of its components. Fraction 5 represents 2.5% of the total recovered fractions. NMR of fractions 4 and 7 confirmed purities between 95 and 100% (spectra not shown).

It is understood that the foregoing detailed description is given merely by way of illustration and that modifications and variations may be made therein without departing from the spirit and scope of the invention.

TABLE 1

Solvent extraction of simmondsin concentrate*

| Solvent | % Extracted by weight | S | SF | DWE | DMS | Total |
| --- | --- | --- | --- | --- | --- | --- |
| Starting concentrate |  | 15.3 | 4.9 | 16.2 | 6.0 | 42.4 |
| Acetone | <1 | — | — | — | — | — |
| Acetonitrile | 1 | — | — | — | — | — |
| Chloroform | 0.1 | — | — | — | — | — |
| Methanol | 95.6 | — | — | — | — | — |
| Water | 100 | — | — | — | — | — |
| Ethanol | 35.6 | 36.3 | 10.1 | 14.4 | 10.6 | 71.5 |
| 5/95 MeOH/CHCl$_3$ | 8.6 | 34.8 | 15.2 | — | — | 50.0 |
| Isopropanol | 16.1 | 35.1 | 4.4 | 3.8 | 1.1 | 43.4 |
| 5/95 Water/isopropanol | 32.4 | 35.8 | 4.8 | 4.4 | 1.7 | 46.7 |

*20:1 Solvent volume: solids weight.

TABLE 2

Extraction of simmondsin concentrate[a] (1.00 g) with isopropanol (IPr)/water combinations

| Ipr/water volume ratio | Solvent/solute ml/g | Extract wt., g | Extract Composition, % | | | |
| --- | --- | --- | --- | --- | --- | --- |
|  |  |  | S | DDMS | DMS | SF |
| 100/0 | 20 | 0.161 | 35.1 | 3.8 | 1.1 | 4.4 |
| 95/5 | 20 | 0.324 | 35.7 | 4.4 | 1.7 | 4.8 |
| 90/10 | 15 | 0.236 | 36.9 | 4.3 | 1.6 | 4.8 |
| 85/15 | 15 | 0.242 | 36.4 | 3.8 | 1.8 | 5.1 |
| 70/30 | 15 | 0.840 | 23.0 | 3.8 | 1.6 | 4.2 |
| 100/0 | 15 | 0.150 | 40.5 | 4.5 | 1.5 | 3.6 |
| 95/5 | 15 | 0.251 | 40.9 | 5.1 | 0.8 | 4.3 |
| 90/10 | 10 | 0.215 | 48.8 | 6.0 | 2.8 | 5.4 |
| 85/15 | 10 | 0.187 | 38.2 | 4.3 | 1.7 | 5.3 |
| 70/30 | 10 | 0.702 | 25.6 | 4.1 | 1.9 | 4.5 |

[a]21.1% S, 11.0% DDMS, 6.22% DMS, 4.06% SF.

TABLE 3

Calculated selectivity[a] for isopropanol (IPr)/water extracts of simmondsin concentrate
(from data in Table 2)

| IPr/water volume ratio | Solvent/solute ml/g | SIMM_X | DDMS_X | DMS_X | SF_X | TOT_X |
|---|---|---|---|---|---|---|
| 100/0 | 20 | 0.446 | 0.019 | 0.005 | 0.189 | 0.177 |
| 95/5 | 20 | 0.928 | 0.050 | 0.024 | 0.453 | 0.392 |
| 90/10 | 15 | 0.720 | 0.036 | 0.018 | 0.329 | 0.298 |
| 85/15 | 15 | 0.720 | 0.029 | 0.021 | 0.380 | 0.299 |
| 70/30 | 15 | 0.998 | 0.100 | 0.056 | 0.896 | 0.497 |
| 100/0 | 15 | 0.553 | 0.025 | 0.003 | 0.118 | 0.210 |
| 95/5 | 15 | 0.943 | 0.053 | 0.004 | 0.280 | 0.365 |
| 90/10 | 10 | 1.16 | 0.063 | 0.043 | 0.378 | 0.475 |
| 85/15 | 10 | 0.613 | 0.028 | 0.014 | 0.317 | 0.255 |
| 70/30 | 10 | 1.03 | 0.097 | 0.066 | 0.854 | 0.510 |

[a]Average of 2 determinations. Selectivity = (concentration in extract/concentration in SC)
(weight in extract/weight in SC).

TABLE 4

Temperature dependence of solubility (g/10 ml) of simmondsin concentrate

| Ethanol/water ratio in solvent | Solvent volume: solute weight | 16° C. | 26° C. | 36° C. |
|---|---|---|---|---|
| 100/0 | 10:1 | 0.270 | 0.286 | 0.345 |
| 95/5 | 5:1 | 0.644 | 0.556 | 0.555 |
| 85/15 | 20:1 | 0.195 | 0.224 | 0.238 |

TABLE 5

Extraction of simmondsins from simmondsin concentrate (SC) with
ethanol then 80/20 ethanol/water

| | Weight, % | S, % | SF, % | DMS, % | DDMS, % | Total, % |
|---|---|---|---|---|---|---|
| SC | 100 | 15 | 5 | 6 | 16 | 42 |
| Ethanol (20:1 vol:wt) | 31 | 50 | 7.1 | 10 | 12 | 80 |
| 80/20 ethanol/water (10:1 vol:wt) | 32 | 8.5 | 4.0 | 5.3 | 23 | 41 |
| Residue | 37 | 3.0 | 1.4 | 2.2 | 9.0 | 16 |

TABLE 6

Preparative HPLC separation of simmondsins

| Fraction no. | Fraction wt., g | Elution time, min | S, % | DDMS, % | DMS, % | SF, % | Total, % |
|---|---|---|---|---|---|---|---|
| 1 | 2.78 | 0–16 | 0.5 | 0 | 0 | 0 | 0.5 |
| 2 | 0.87 | 16–18 | 0.0 | 62.4 | 29.2 | 0 | 91.6 |
| 3 | 0.73 | 18–20 | 21 | 0.7 | 78.2 | 0 | 99.2 |
| 4 | 3.60 | 20–26 | 100 | 0 | 0 | 0 | 100 |
| 5 | 0.23 | 26–34 | 10 | 0 | 0.2 | 0 | 10.2 |
| 6 | 0.35 | 34–40 | 1.4 | 1.3 | 5.0 | 35 | 42 |
| 7 | .52 | 40–45 | 3.0 | 0 | 0 | 97 | 100 |
| 8 | .024 | 45–50 | 1.2 | 0 | 0 | 40.7 | 41.9 |

We claim:

1. A process for isolation of simmondsins from jojoba meal comprising:

a) providing a solid phase, dried water extract of defatted jojoba meal, b) contacting said water extract with a first solvent comprising ethanol effective to extract simmondsins from said solid phase water extract and form a first solvent fraction comprising said first solvent and simmondsins, and c) separating said first solvent fraction from said solid phase.

2. The process of claim 1 wherein said first solvent comprises a mixture of ethanol and water and the ethanol concentration is at least about 80%.

3. The process of claim 1 wherein said first solvent comprises a mixture of ethanol and water wherein the concentration of ethanol is at least about 95% ethanol.

4. The process of claim 1 wherein said first solvent comprises approximately 100% ethanol.

5. The process of claim 4 wherein said first solvent comprises absolute ethanol.

6. The process of claim 1 further comprising separating said simmondsins from said first solvent fraction from (c) by reverse phase high pressure liquid chromatography.

7. The process of claim 6 wherein said high pressure liquid chromatography comprises eluting said first solvent fraction from (c) with a sequence of 100% water, followed by a 50:50 mixture of water and ethanol, followed by absolute ethanol.

8. The process of claim 1 further comprising removing said first solvent from said first solvent fraction from (c).

9. The process of claim 8 wherein said removing comprises drying said first solvent fraction from (c) to a solid.

10. The process of claim 1 wherein said solid phase, dried water extract of defatted jojoba meal is prepared by:

I) contacting defatted jojoba meal with water under conditions effective to extract simmondsins from said meal and form a water extract comprising water and simmondsins, II) separating said water extract from said meal, and III) removing said water from said water extract to form a solid phase, dried water extract comprising simmondsins.

11. The process of claim 1 wherein said simmondsins comprise simmondsin, simmondsin ferulate, demethylsimmondsin, and didemethyl simmondsin.

12. The process of claim 4 further comprising:
d) contacting said solid phase from (c) with a second solvent effective to extract residual simmondsins from said solid phase and form a second solvent fraction comprising said second solvent and simmondsins, said second solvent comprising a solution of about 80% ethanol and about 20% water, and
e) separating said second solvent fraction from said solid phase.

13. The process of claim 12 further comprising removing said second solvent from said second solvent fraction from (e).

14. The process of claim 13 wherein said removing comprises drying said second solvent fraction from (e) to a solid.

* * * * *